(12) United States Patent
Zhang et al.

(10) Patent No.: US 6,989,451 B2
(45) Date of Patent: Jan. 24, 2006

(54) HETEROCYCLIC COMPOUNDS AND USES THEREOF

(75) Inventors: Weijian Zhang, Irvine, CA (US); William Ricketts, Irvine, CA (US); Haoyun An, Carlsbad, CA (US); Zhi Hong, Aliso Viejo, CA (US)

(73) Assignee: Valeant Research & Development, Costa Mesa, CA (US)

( * ) Notice: Subject to any disclaimer, the term of this patent is extended or adjusted under 35 U.S.C. 154(b) by 0 days.

(21) Appl. No.: 10/455,149

(22) Filed: Jun. 4, 2003

(65) Prior Publication Data

US 2004/0039037 A1   Feb. 26, 2004

Related U.S. Application Data

(60) Provisional application No. 60/386,175, filed on Jun. 4, 2002.

(51) Int. Cl.
 *C07D 275/03*   (2006.01)
 *A61K 31/425*   (2006.01)

(52) U.S. Cl. .................. 548/206; 548/213; 548/214; 514/372

(58) Field of Classification Search ............... 548/206, 548/213, 214
 See application file for complete search history.

(56) References Cited

U.S. PATENT DOCUMENTS

| | | | |
|---|---|---|---|
| 3,155,678 A * | 11/1964 | Hatchard | .................... 548/214 |
| 4,560,695 A | 12/1985 | Hirsch et al. | |
| 5,298,515 A * | 3/1994 | Schubert et al. | ............ 514/361 |
| 5,578,622 A | 11/1996 | Ikeda et al. | |
| 6,235,764 B1 | 5/2001 | Larson et al. | |
| 6,380,214 B1 | 4/2002 | Gant et al. | |
| 6,548,526 B2 | 4/2003 | Larson et al. | |

OTHER PUBLICATIONS

CA Registry No. 348137-52-0, entry date into Registry file on STN is Jul. 25, 2001.*
CA Registry No. 348137-51-9, entry date into Registry file on STN is Jul. 25, 2001.*
Brown et al., Science of Synthesis (Apr. 2002), 11, pp. 507-572.*
Schaefer, Journal fuer Praktische Chemie (Leipzig) (1987), 329(2), pp. 355-358.*
Goerdeler et al., Chemische Berichle (1964), pp. 3106-3117.*
Hatchard, Journal of Organic Chemistry (1964), 29(3), pp. 660-665.*
CA Registry No. 287196-73-0, entry date into Registry file on STN is Aug. 24, 2000.*
C.J. Shishoo, et al., "A Facile Synthesis of 3-Amino-5-substitutedaminiothiazole-4-carboxylic Acid Derivatives," Dept. of Pharm. Chem., L.M. College of Pharmacy, p. 759-765, (Aug. 29, 1987).

* cited by examiner

*Primary Examiner*—Laura L. Stockton
(74) *Attorney, Agent, or Firm*—Brown Raysman Millstein Felder & Steiner

(57) ABSTRACT

Substituted isothiazole compounds and compositions are provided, wherein particularly preferred compositions and methods are directed towards inhibition of various protein kinases (especially MEK and/or ERK). Consequently, particularly preferred methods include treatment of diseases associated with abnormality in MEK and/or ERK function.

2 Claims, No Drawings

HETEROCYCLIC COMPOUNDS AND USES THEREOF

This application claims the benefit of U.S. provisional application No. 60/386,175, filed Jun. 4, 2002, which is incorporated herein by reference.

FIELD OF THE INVENTION

The present invention relates to heterocyclic compounds, and especially to heterocyclic compounds with protein kinase inhibitor activity and their use in pharmaceutical compositions containing such compounds (e.g., as antineoplastic agents).

BACKGROUND OF THE INVENTION

Mammalian cells utilize signaling pathways to regulate various processes, especially cell growth and cell cycling. For example, the mitogen-activated protein kinase (MAPK) pathway (also known as Raf-MEK-ERK phosphorylation cascade) transfers signals from growth factors and hormones binding at cell surface receptors to transcription factors in the nucleus to control gene expression and other cellular functions [Seeger, R. et al., FASEB J. 1995, 9, 726; Cobb, M. H. et al., J Biol. Chem. 1995, 270, 14843; Schaeffer, H. J. et al., Mol. Cell. Biol. 1999, 19, 2435; Garrington, T. P. et al., Curr. Opin Cell. Biol. 1999, 11, 211]. Aberrant signal transduction via signaling pathways that are responsible for the regulation of cell growth and division has been shown to cause uncontrolled cell growth or cancer.

It is known that MAPK kinases (MEK) are important components in the MAPK pathway for regulating diverse cellular events, including cell transformation, proliferation, differentiation, and/or apoptosis. MEK and ERK (extracellular signal regulated protein kinase, or MAP kinase) are frequently dysregulated in human cancers [Oka, H. et al., Cancer Res. 1995, 55, 4182; Sivaraman, V. S. et al., J. Clin. Invest. 1997, 99, 1478; Hoshino, R. et al., Oncogene 1999, 18, 813] and have been recognized as potential drug targets for therapeutic intervention in the treatment of cancer, inflammation, leukemia, and other diseases [Stein, B. et al., Annu. Rep. Med. Chem. 1996, 31, 289; Sedlacek, H. H. Drugs 2000, 59, 435; Levitt, M. L. et al., Invest. New Drugs 1999, 17, 213; Cohen, P., Curr. Opin. Chem. Biol. 1999, 3, 459; Levitzki, A. Pharmacol., Ther. 1999, 82, 231]. In other examples, constitutively active MEK mutants are known to induce cell transformation and produce tumors in nude mice [Brunet, A. et al., Oncogene 1994, 9, 3379; Cowley, S. at el., J. Cell 1994, 77, 841; Mansour, S. J. et al., Science 1994, 265, 966]. In still further examples, over-expression and/or over-activation of MEK (or its substrate ERK) protein have also been found to be associated with various human cancers, including kidney, breast, colon, and oral carcinomas, leukemia, and glial neoplasmas [Oka, H. et al., Cancer Res. 1995, 55, 4182; Sivaraman, V. S. et al., J. Clin. Invest. 1997, 99, 1478; Kono, Y. et al., Jpn. J. Cancer Res. 1998, 89, 903; Towatari, M. et al., Leukemia 1997, 11, 479; Mandell, J. W. et al., Am. J Pathol. 1998, 153, 1411].

Thus, it is believed that inhibitors of the MAPK pathway, and especially inhibitors of MEK and/or ERK may serve as selective inhibitors of the growth of mammalian cancer cells. There are numerous such inhibitors known in the art, and exemplary classes of inhibitors are described in U.S. Pat. Nos. 6,440,966 and 6,506,798 to Barrett et al. Here, the inventors employ selected benzenesulfonamide derivatives, and various 4-arylamino, 4-aryloxy, and 4-arylthio diarylamines, respectively, as MEK inhibitors. Larson and Gant describe in U.S. Pat. Nos. 6,235,764, 6,548,526, and 6,380,214, respectively, various isothiazole compounds which exhibit some similarity in structure to Barrett's compounds. However, the inventors report biological activity only on neovascularisation, but not on MEK/ERK inhibition. Further known isothiazole compounds include those described by Shishoo et al. (Journal of Heterocyclic Chemistry 1988, 25(3): 759–65) and U.S. Pat. No. 3,230,229 to Hatchard, but none of these references teaches kinase inhibition using such compounds. In still another example, Boschelli et al. describe, in U.S. Pat. No. 6,521,618, various 3-cyanoquinolines, 3-cyano-1,6-naphthyridines and 3-cyano-1,7-naphthyridines as selective MEK inhibitors.

While certain isothiazole compounds are known to exhibit kinase inhibitory effects, selectivity towards MEK and/or ERK and specificity to inhibit malignant cells remains often problematic. Furthermore, toxicity of such known MEK or ERK inhibitors is often encountered, especially at higher concentrations. Thus, there is still a need to provide improved compositions and methods of inhibiting protein kinases, and especially MEK and/or ERK.

SUMMARY OF THE INVENTION

The present invention is generally directed towards various heterocyclic compounds, and more preferably to substituted isothiazole compounds in which the isothiazole ring is covalently bound to an aromatic system (e.g., phenyl or naphtyl, optionally substituted) via an NH group, and wherein such compounds exhibit a selective inhibitory effect on MEK and/or ERK. Consequently, it should be recognized that such compounds might be advantageously used in the treatment of various diseases that are associated with dysregulation of MEK and/or ERK (e.g., neoplastic and other proliferative diseases, including inflammation, psoriasis, and restenosis, asthma, stroke, heart failure, and immunodeficiency disorders). Furthermore, contemplated compounds may also be used as precursors or intermediates for the synthesis of other pharmaceutically active molecules (especially including amidines).

In one preferred aspect of the inventive subject matter, contemplated compounds will generally have a structure according to Formula 1, wherein the substituents are as described in the detailed description below, and especially preferred compounds include those in which Z is S, X is N, W is NH, $R_2$ is a phenyl group or naphtyl group (optionally substituted with one to three substituents), Y—$R_1$ is OH, and V is CN, C(O)NH, C(NH)NH$_2$, CH$_2$OH, or CHO.

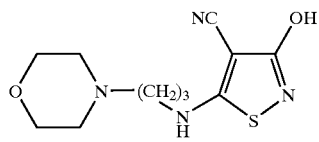

In another preferred aspect of the inventive subject matter, contemplated compounds will be included in a pharmaceutical composition at a concentration effective to inhibit MEK/ERK. Therefore, such pharmaceutical compositions are thought to be effective in treating disorders associated with dysregulation of MEK and/or ERK.

Various objects, features, aspects and advantages of the present invention will become more apparent from the following detailed description of preferred embodiments of the invention.

DETAILED DESCRIPTION

The inventors discovered that various heterocyclic compounds, and especially isothiazole derivatives exhibit potent inhibitory action on protein kinases, and particularly on those in the mitogen-activated protein kinase (MAPK) pathway. Consequently, numerous heterocyclic compounds and their uses are contemplated herein.

As used herein, the terms "halo" and "halogen" are used interchangeably herein and refer to fluoro, chloro, bromo, and/or iodo groups. As further used herein, the terms "alkyl" and "unsubstituted alkyl" are used interchangeably herein and refer to any linear, branched, or cyclic hydrocarbon in which all carbon-carbon bonds are single bonds. The terms "alkenyl" and "unsubstituted alkenyl" are used interchangeably herein and refer to any linear, branched, or cyclic alkyl with at least one carbon-carbon double bond. Furthermore, the terms "alkynyl" and "unsubstituted alkynyl" are used interchangeably herein and refer to any linear, branched, or cyclic alkyl or alkenyl with at least one carbon-carbon triple bond. The terms "aryl" and "unsubstituted aryl" are used interchangeably herein and refer to any aromatic cyclic alkenyl or alkynyl. The term "alkaryl" is employed where an aryl is covalently bound to an alkyl, alkenyl, or alkynyl, and the term "alkoxy" refers to a substituted or unsubstituted alkyl, alkenyl, or alkynyl that is covalently bound to an oxygen.

As further used herein, the term "4–10 membered heterocyclic" refers to monocyclic, bicyclic, and tricyclic aromatic and non-aromatic groups containing one or more heteroatoms (e.g., O, S, or N) in at least one ring. The term "heteroaryl" refers to a group that includes at least one aromatic ring in which at least one heteroatom is present.

The term "substituted" as used herein refers to a replacement or modification of an atom (radical) or chemical group (e.g., H, $NH_2$, or OH) in a molecule with a functional group to produce a-substituted molecule, and particularly contemplated functional groups include nucleophilic groups (e.g., $—NH_2$, —OH, —SH, —NC, etc.), electrophilic groups (e.g., C(O)OR, C(X)OH, etc.), polar groups (e.g., —OH), non-polar groups (e.g., aryl, alkyl, alkenyl, alkynyl, etc.), ionic groups (e.g., $—NH_3^+$), and halogens (e.g., —F, —Cl), and all chemically reasonable combinations thereof. For example, where the molecule is an alkyl, the replaced radical is a hydrogen radical, and the functional group is a hydroxyl group, the H-atom is substituted by an OH group to form a substituted alkyl. In another example, where the molecule is an amino acid, the modified group is the amino group, and the functional group is an alkyl group, the amino group is alkylated to form an N-substituted amino acid.

Contemplated Compounds

Generally contemplated compounds will have a structure according to Formula 1 below:

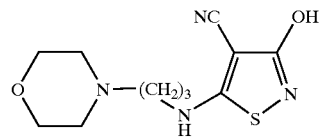

wherein Z is S, O, or $NR_3$; X is N or $CR_4$; Y is O, S, S(O), $S(O)_2$, $NR_3$, or $CR_3R_4$, or Y is a covalent bond where $R_1$ is a halogen, —COOH, $—NO_2$, $—N_3$, —CN, $—SO_3H$, or $—CF_3$; W is S, O, $NR_1$, or $NR_3$; V is V is —CN, $—C(NR_3)$ $NR_4R_5$, $—C(NR_3)SR_4$, $—C(NR_3)SR_4$, $—C(O)NR_3R_4$, $—CO_2R_3$, $—CH(OR_3)(OR_4)$, $—C(O)R_3$, $—CR_3R_4R_5$, $—CH_2NR_3R_4$, $—NR_3R_4$, $—NR_3SO_2R_4$, $—SO_2NR_3R_4$, $—NR_3C(O)R_4$ or a C6–C10 aryl, a 4–10 membered heterocyclic group containing 1–4 heteroatoms (e.g., N, O, S, or $SO_2$), C1–C10 alkyl, C2–C10 alkenyl, C2–C10 alkynyl, $—(CH2)n-R3$, where n is an integer from 0 to 5; said alkyl group optionally includes 1 or 2 hetero moieties selected from O, S, and $—N(R_3)—$; each of the forgoing $R_3$ and $R_4$ may be taken together with Y or $R_1$ to form a 5 to 6 membered unsaturated or partially saturated ring or a 5 to 6 membered heteroaryl ring, where said unsaturated or partially saturated or heteroaryl ring may include 1 to 3 heteroatoms (e.g., O, S, =N— or —N=, or $—N(R_3)—$) in addition to Y, where said unsaturated or partially saturated or heteroaryl rings, including the $R_3$ group of the said $—N(R_3)—$, are optionally substituted by 1 to 5 $R_5$ groups;

$R_1$ is H, C1–C10 alkyl, C2–C10 alkenyl, C2–C10 alkynyl, $—CR_3R_4OC(O)R_5$, $—C(O)R_3$, $—C(O)OR_3$, $—C(O)NR_3R_4$, $—(CH_2)_n$(C6–C10 aryl), or $—(CH_2)_n$(C5–C10 membered heterocyclic group), where n is an integer from 0 to 5; wherein the alkyl optionally includes 1 or 2 hetero moieties (e.g., O, S, or $—N(R_5)—$); wherein the aryl and/or heterocyclic group is optionally fused to a C6–C10 aryl group, a C5–C8 saturated cyclic group, or a 4–10 membered heterocyclic group; and wherein $R_1$ is optionally substituted (preferably with 1 to 5 $R_5$);

$R_2$ is H, $C_1$–$C_{10}$ alkyl, $C_2$–$C_{10}$ alkenyl, $C_2$–$C_{10}$ alkynyl, $—C(O)(C_1$–$C_{10}$ alkyl), $—C(O)(C_1$–$C_{10}$ aryl), $—(CH_2)_n$($C_6$–$C_{10}$ aryl), or $—(CH_2)_n$($C_5$–$C_8$ membered heterocyclic), where n is an integer from 0 to 5; wherein the alkyl optionally includes 1 or 2 hetero moieties (e.g., O, S, or $—N(R_5)—$); wherein the aryl and/or heterocyclic group is optionally fused to a $C_6$–$C_{10}$ aryl group, a $C_5$–$C_8$ saturated cyclic group, or a 4–10 membered heterocyclic group; and wherein $R_1$ is optionally substituted (preferably with 1 to 5 $R_5$);

$R_3$ is H, $C_5$–$C_{10}$ aryl, 4–10 membered heterocyclic groups, where said heterocyclic groups may include 1 to 3 heteroatoms (e.g., O, S, $—N(R_1)$, =N—, or —N=); wherein the aryl and/or heterocyclic group are optionally fused to a $C_6$–$C_{10}$ aryl group, a $C_5$–$C_8$ saturated cyclic group, or a 4–10 membered heterocyclic group; wherein the heterocyclic ring may include 1 to 3 heteroatoms (e.g., O, S, $—N(R_1)$, =N—, or —N=); and wherein up to five carbon atoms in the aryl or heterocyclic moieties are optionally substituted (preferably with 1 to 5 $R_5$);

$R_4$ is H or $C_1$–$C_6$ alkyl and may be taken together with Y or $R_1$ to form a 5 or 6 membered saturated ring or a 5 or 6 membered heteroaryl ring, wherein the saturated and/or heteroaryl ring may include 1 to 3 heteroatoms in addition to Y (e.g., O, S, $—N(R_1)$, =N—, or —N=); and wherein the saturated ring may contain 1 or 2 carbon-carbon double bonds and wherein the saturated and/or heteroaryl ring, including the $R_1$ group of the $—N(R_1)—$, are optionally substituted (preferably with 1 to 5 $R_5$);

$R_5$ is H, $C_1$–$C_{10}$ alkyl, $C_2$–$C_{10}$ alkenyl, $C_2$–$C_{10}$ alkynyl, $C_1$–$C_6$ hydroxyalkyl, halomethyl, C2–C7 alkoxymethyl, $C_2$–$C_7$ carboalkoxy, $C_2$–$C_7$ carboalkyl, benzoyl, benzyl, $C_1$–$C_6$ alkylamnino, $C_2$–$C_{12}$ dialkylamino, benzylamino, $C_6$–$C_{10}$ aryl group, 4–10 membered heterocyclic group, halo, cyano, nitro, trifluoromethyl, trifluoromethoxy, azide, —$OR_6$, $N_3$, CN, —$C(O)R_6$, —$C(O)OR_6$, —$NR_6C(O)R_7$, —$OC(O)R_6$, —$C(O)NR_6R_7$, —$NR_6R_7$, —$S(O)_jR_6$ and $N(O)_j$ where j is an integer from 0 to 2, or $SO_3H$;

$R_6$ and $R_7$ are independently H, $C_1$–$C_{10}$ alkyl, $C_2$–$C_{10}$ alkenyl, $C_2$–$C_{10}$ alkynyl, $C_6$–$C_{10}$ aryl group, 4–10 membered heterocyclic group, wherein the aryl and heterocyclic group is optionally substituted with 1–3 substituents (e.g., alkyl, cyano, nitro, trifluoromethyl, trifluoromethoxy, halo, azido, —$OR_8$, —$C(O)R_8$, —$C(O)OR_8$, —$NR_8C(O)R_9$, —$OC(O)R_8$, —$C(O)NR_8R_9$, —$NR_8R_9$, —$S(O)_jR_8$ or $N(O)_j$ where j is an integer from 0 to 2, —$SO_3H$), and wherein $R_6$ and $R_7$ may be taken together to form a fused ring;

$R_8$ and $R_9$ are independently H, $C_1$–$C_{10}$ alkyl, $C_2$–$C_{10}$ alkenyl, $C_2$–$C_{10}$ alkynyl, $C_1$–$C_6$ hydroxyalkyl, halomethyl, $C_2$–$C_7$ alkoxymethyl, $C_2$–$C_7$ benzyl, $C_6$–$C_{10}$ aryl group, 4–10 membered heterocyclic group.

Particularly preferred compounds include those of Formula 2

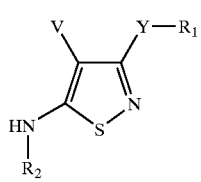

Formula 2 wherein $R_2$ is a group that is covalently bound to the nitrogen atom of the NH group via an atom or group other than a C=O group, and is most preferably an optionally substituted phenyl group or naphthalen-1-yl group. Particularly preferred substituents for the phenyl and/or naphthyl group include $C_1$–$C_{10}$ alkyl, $C_2$–$C_{10}$ alkenyl, $C_2$–$C_{10}$ alkynyl, $C_6$–$C_{10}$ aryl group, a 4–10 membered heterocyclic group, wherein the aryl group and/or heterocyclic group is optionally substituted (e.g., with alkyl, halo, cyano, nitro, trifluoromethyl, trifluoromethoxy, azido, —$SO_3H$, —$OR_8$, —$C(O)R_8$, —$C(O)OR_8$, —$NR_8C(O)R_9$, —$OC(O)R_8$, —$C(O)NR_8R_9$, —$NR_8R_9$, —$S(O)_jR_8$ and $N(O)_j$ where j is an integer from 0 to 2).

Further particularly preferred compounds according to Formulae 1 and 2 will include those in which V is CN, $C(O)NH_2$, or $C(NH)NH_2$, and/or in which $YR_1$ is OH or $NH_2$, and/or in which $R_2$ is a substituted phenyl or an optionally substituted naphtyl (e.g., substituted with an alkyl, a halogen, a hydroxyl, or an acyl). Exemplary preferred compounds will therefore particularly include: 5-(4-Chloro-phenylamino)-3-hydroxy-isothiazole-4-carbonitrile; 5-(3-Chloro-phenylamino)-3-hydroxy-isothiazole-4-carbonitrile; 5-(2-Chloro-phenylamino)-3-hydroxy-isothiazole-4-carbonitrile; 5-(4-Bromo-phenylamino)-3-hydroxy-isothiazole-4-carbonitrile; 5-(3-Bromo-phenylamino)-3-hydroxy-isothiazole-4-carbonitrile; 5-(2-Bromo-phenylamino)-3-hydroxy-isothiazole-4-carbonitrile; 5-(4-Fluoro-phenylamino)-3-hydroxy-isothiazole-4-carbonitrile; 5-(3-Fluoro-phenylamino)-3-hydroxy-isothiazole-4-carbonitrile; 5-(2-Fluoro-phenylamino)-3-hydroxy-isothiazole-4-carbonitrile; 3-Hydroxy-5-(4-isopropyl-phenylamino)-isothiazole-4-carbonitrile; 3-Hydroxy-5-(m-tolylamino)-isothiazole-4-carbonitrile; 3-Hydroxy-5-(4-nitro-phenylamino)-isothiazole-4-carbonitrile; 5-(4-Acetyl-phenylamino)-3-hydroxy-isothiazole-4-carbonitrile; 3-Hydroxy-5-(naphthalen-1-ylamino)-isothiazole-4-carbonitrile; 3-Hydroxy-5-(3-methoxy-biphenyl-4-ylamino)-isothiazole-4-carbonitrile; 5-(2-Dimethylamino-naphthalen-1-ylamino)-3-hydroxy-isothiazole-4-carbonitrile; 5-(4-Dimethylamino-naphthalen-1-ylamino)-3-hydroxy-isothiazole-4-carbonitrile; 3-Hydroxy-5-(2-trifluoromethyl-phenylmino)-isothiazole-4-carbonitrile; 3-Amino-5-(4-methyl-phenylmino)-isothiazole-4-carbonitrile; 5-(4-Amino-phenylmino)-3-hydroxy-isothiazole-4-carbonitrile; 5-(4-Chloro-3-trifluoromethyl-phenylmino)-3-hydroxy-isothiazole-4-carbonitrile; 3-Hydroxy-5-(4-methoxycarbonyl-phenylmino)-isothiazole-4-carbonitrile; 3-Hydroxy-5-(2-methoxycarbonyl-phenylmino)-isothiazole-4-carbonitrile; 5-(2,4-Dichloro-phenylmino)-3-hydroxy-isothiazole-4-carbonitrile; 5-(3,5-Dichloro-phenylmino)-3-hydroxy-isothiazole-4-carbonitrile; 3-Hydroxy-5-(indan-1-ylmino)-isothiazole-4-carbonitrile; 5-(3,5-Dichloro-phenylmino)-3-hydroxy-isothiazole-4-carbonitrile; 3-Hydroxy-5-(tetrahydro-furan-2-yl)-isothiazole-4-carbonitrile; 3-Hydroxy-5-piperidino-isothiazole-4-carbonitrile; 5-n-Butylmino-3-hydroxy-isothiazole-4-carbonitrile; 5-n-Butylmino-3-hydroxy-isothiazole-4-carbonitrile; 3-Hydroxy-5-[2-(4-hydroxy-phenyl)-ethylamino]-isothiazole-4-carbonitrile; 3-Hydroxy-5-(4-phenoxy-phenylamino)-isothiazole-4-carboxamidine; 3-Hydroxy-5-(4-phenoxy-phenylamino)-isothiazole-4-carboxamide; 3-Cyclohexyloxy-5-(phenylamino)-isothiazole-4-carbonitrile; 3-Hydroxy-5-(3-morpholin-4-yl-propylamino)-isothiazole-4-carbonitrile; 3-Hydroxy-5-(4-styryl-phenylamino)-isothiazole-4-carbonitrile; 5-(3-Cyano-phenylamino)-3-hydroxy-isothiazole-4-carbonitrile; 4-(4-Cyano-3-hydroxy-isothiazol-5-ylamino)-N-phenyl-benzamide; 3-Hydroxy-5-(2-methoxy-dibenzofuran-3-ylamino)-isothiazole-4-carbonitrile; 4-(4-Cyaco-3-hydroxy-isothiazol-5-ylamino)-N-phenyl-benzenesulfonamide; 5-(2,4-Dichloro-phenylamino)-3-hydroxy-isothiazole-4-carbonitrile; 5-(2,3-Dichloro-phenylamino)-3-hydroxy--isothiazole-4-carbonitrile; 5-(4-Benzoyl-phenylamino)-3-hydroxy-isothiazole-4-carbonitrile; 3-Hydroxy-5-(4-phenylamino-phenylamino)-isothiazole-4-carbonitrile; 5-[4-(4-Bromophenylamino)-phenylamino]-3-hydroxy-isothiazole-4-carbonitrile; 3-Hydroxy-5-(4-phenylazo)-phenylamino)-isothiazole-4-carbonitrile; 5-(4-Benzyl-phenylamino)-3-hydroxy-isothiazole-4-carbonitrile; 5-(n-Butylamino)-3-hydroxy-isothiazole-4-carbonitrile; 3-Hydroxy-5-[2-(4-hydroxy-phenyl)-ethylamino]-isothiazole-4-carbonitrile; 3-Hydroxy-5-(3-methoxy-propylamino)-isothiazole-4-carbonitrile; 5-Fufuryl-3-hydroxy-isothiazole-4-carbonitrile; 3-Hydroxy-5-(4-methoxy-benzylamino)-isothiazole-4-carbonitrile; 5-[4-(4-Chloro-phenoxy)-3-hydroxy-phenylamino]-isothiazole-4-carbonitrile; 5-[4-(4-Fluoro-phenoxy)-3-hydroxy-phenylamino]-isothiazole-4-carbonitrile; 3-Hydroxy-5-[4-(4-methoxy-phenoxy)-phenylamino]-isothiazole-4-carbonitrile; 3-Benzylamino-5-phenylamino-isothiazol-4-carbonitrile; 3-Amino-5-phenylamino-isothiazol-4-carbonitrile.

It should be noted that some of the compounds per se as described herein are known, and that such selected compounds are known as fungicidal and/or bactericidal agents with little or no toxicity to human or plants (see e.g., U.S. Pat. No. 5,578,622 to Ikeda et al.). Such compounds per se are expressly excluded from the contemplated compounds described above. However, it has not been previously appreciated that the contemplated compounds are active against mammalian cells and/or MEK or ERK kinases, and especially against mammalian cells with dysregulated MEK or ERK kinases. Therefore, and at least to the extent as to which contemplated compounds are known per se, it should be recognized that the specific use as a MEK or ERK inhibitors still falls within the scope of the inventive subject matter presented herein.

In further contemplated aspects of the inventive subject matter, it should be appreciated that the compounds according to the inventive subject matter may be present in various isomeric forms, and all of the possible isomeric forms are specifically included herein. For example, where appropriate, the compounds may be present as diastereomers or enantiomers, and all diastereomeric and enantiomeric forms are considered herein. Moreover, where the compounds include one or more chiral centers, all configurations and combinations thereof are contemplated as either optically pure compounds. or as racemic mixtures. The compounds of Formulae 1 and 2 may also exist as tautomers, and it should be appreciated that all tautomeric forms are specifically contemplated herein. Still further, contemplated compounds additionally include isotope labeled compounds, in which at least one atom is replaced by an atom having the same atomic number but a different mass number (suitable isotopes may be stable or decay with concomitant emission of energy).

Moreover, it should be recognized that, where desired, contemplated compounds might also be prepared as pharmaceutically acceptable salts. The term "pharmaceutically acceptable salt", as used herein includes salts of acids or bases. For example, certain compounds of Formula 1 and/or 2 are basic and may form a variety of salts with various inorganic and organic (most preferably non-toxic) acids. Therefore, compounds according to Formula 1 and/or Formula 2 may form additional salts containing pharmaceutically acceptable anions. Suitable anions include chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccarate, formate, benzoate, glutamate, methasulfonate, enthanesulfonate, benzenesulfonate, p-toluenesulfonate, and pamoate [i.e., 1,1'-methylene-bis-(2-hydroxy-3-naphthoate)].

Similarly, certain compounds of Formula 1 and/or Formula 2 are acidic and may form a variety of salts with various inorganic and organic (most preferably non-toxic) bases. Therefore, compounds according to Formula 1 and/or Formula 2 may form additional salts containing pharmaceutically acceptable cations. Suitable cations include alkali metal or alkaline earth metal cations, and particularly, sodium and potassium cations.

Of course it should further be recognized that all prodrugs and metabolites of the compounds according to Structures 1 and 2 are also contemplated. Especially preferred prodrugs are those that deliver a contemplated compound to a target cell (e.g., a diseased cell) or target organ (e.g., a diseased organ), wherein the prodrug form may be converted within a cell, organ, or other body compartment in an enzymatic or non-enzymatic manner. Further preferred prodrugs particularly include those in which the prodrug form is less active as compared to the corresponding non-prodrug form. There are numerous prodrug forms for heterocyclic compounds known in the art, and all of the known prodrug forms are considered suitable for use herein.

For example, where available a carboxyl group of contemplated compounds may be derivatized to form the corresponding amide or ester. In another example, a hydroxy group may be derivatized to form the corresponding hemisuccinates, esters, dimethylaminoacetates, or phosphoryloxymethyloxycarbonyls, as outlined in D. Fleisher et al. (*Advanced Drug Delivery Reviews* (1996) 19, 115). In yet further examples, carbamate prodrugs of hydroxy and amino groups are also contemplated, as are carbonate prodrugs and sulfate esters of hydroxy groups. Similarly, derivatization of a hydroxy group to form the corresponding (acyloxy)methyl and (acyloxy)ethyl ethers the acyl group may be an optionally substituted alkyl ester, or the acyl group may be an amino acid ester; see e.g., R. P. Robinson et al., *J. Medicinal Chemistry* (1996) 39, 10) is also contemplated.

With respect to the metabolite, it should be recognized that metabolites of contemplated compounds might be formed by one or more enzymatic reactions (e.g., via hydrolysis, oxidation, reduction, lyase, or ligase reaction, or even via a polymerase action), or via non-enzymatic reactions (e.g., acid hydrolysis, reduction).

Therefore, the inventors contemplate a pharmaceutical composition that includes a compound according to Formula 1 or Formula 2 at a concentration effective to inhibit a kinase (preferably MEK or ERK) of a mammalian cell. In especially preferred compositions, R is a substituted phenyl or an optionally substituted naphtyl, and/or V is CN, $C(O)NH_2$, or $C(NH)NH_2$, and it is still further preferred that the compound further reduces growth of a neoplastic cell in a mammal.

Synthesis of Contemplated Compounds

It is generally contemplated that the compounds according to the inventive subject matter can be prepared using various synthetic strategies, and suitable strategies especially include combinatorial chemistry approaches (on solid phase or in solution) as well as traditional synthetic approaches in which the compounds are separately prepared. Still further contemplated approaches include those in which one or more commercially available compounds (e.g., various substituted isothiazoles) are modified to yield the compounds according to the inventive subject matter. Alternatively, as depicted in the exemplary schemes 1–4 below, reacting suitable compounds with each other under conditions that allow cyclization to the heterocyclic ring may also form the isothiazole ring system.

Scheme 1 illustrates a reaction of 2-cyanoacetamide with an isothiocyanate to an intermediate, and subsequent ring closure by oxidation followed by alkylation or acylation with an R containing reagent (e.g., chloromethyl pivalate [$R=CH_2OC(O)CH(CH_3)_3$] or pivalic acid [$R=C(O)CH(CH3)_3$]) to provide the product 5.

More specifically, in step 1, 2-cyanoacetamide 1 was treated with a strong base (e.g., KOH) and then reacted with a substituted phenyl isothiocyanate in N, N'-dimethylformamide (DMF) at a temperature ranging from −10° C. to 60° C., preferably at 25° C. for a period of about 8 to 24 hours, preferably 16 hours. In step 2, compound 3 (in the same reaction vessel as step 1) was treated at about 0° C. with aqueous chloramine solution for about 12 hours. Alternatively, the reaction mixture of step 1 was concentrated and diluted with water, followed by acidification with hydrochloric acid aqueous solution. Filtration and washing with water afforded compound 3. In an organic solvent, preferably ethyl acetate, compound 3 was treated with bromine to provide the ring closure product compound 4. In step 3 of Scheme 1, compound 4 was treated with an alkylacyloxy methyl chloride, preferably chloromethyl pivalate. The final product 5 was then isolated.

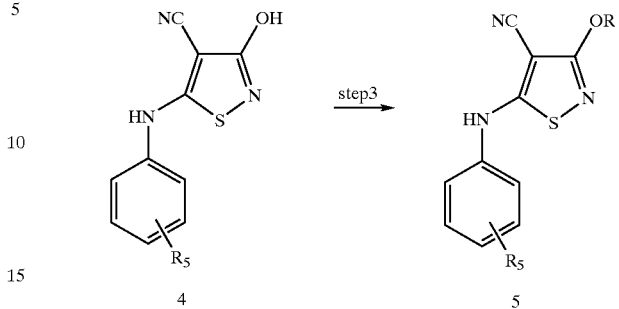

Scheme 2 illustrates an exemplary modification of the cyano group on the isothiazole ring to provide compounds that include a substituent other than a CN group in the 4-position. Here, the cyano group of compound 7 may be hydrolyzed with a strong acid or base to the corresponding carboxamide compound 6. Alternatively, compound 7 may also be converted with selected alcohols in the presence of a strong acid to the corresponding amide compound 8 as described in more detail below, or to the corresponding amidine compound 8 by reacting it with an amine.

Compound 7 may also be reduced to an aldehyde compound 10 with a reducing agent, for example, diisobutylaluminum hydride. The so prepared aldehyde compound 10 may be further reduced to the corresponding alcohol compound 11, or converted to an alkene derivative 9 using Wittig reaction conditions. Alternatively, compound 10 may also be reacted with an alcohol using a strong acid as a catalyst to give dialkyl acetal compound 13, or converted to amine compound 12 using reductive amination conditions.

Similarly, where desirable, the hydroxy group on the isothiazole ring may be alkylated with an alkyl halide or acylated with an acid chloride, and then the hydroxymethyl group may be alkylated or acylated in a similar manner as above to give the ether or diester compound 14.

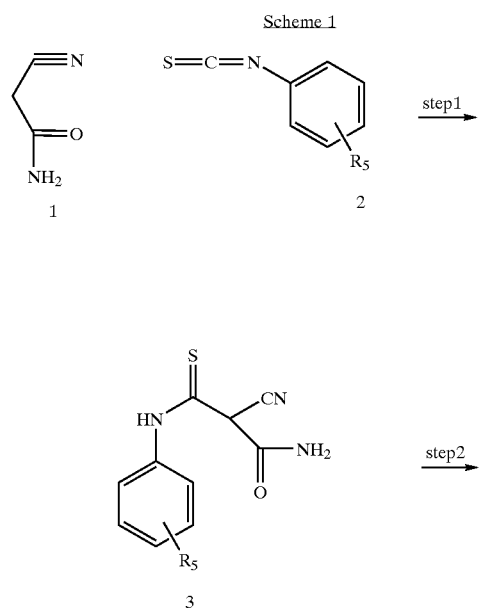

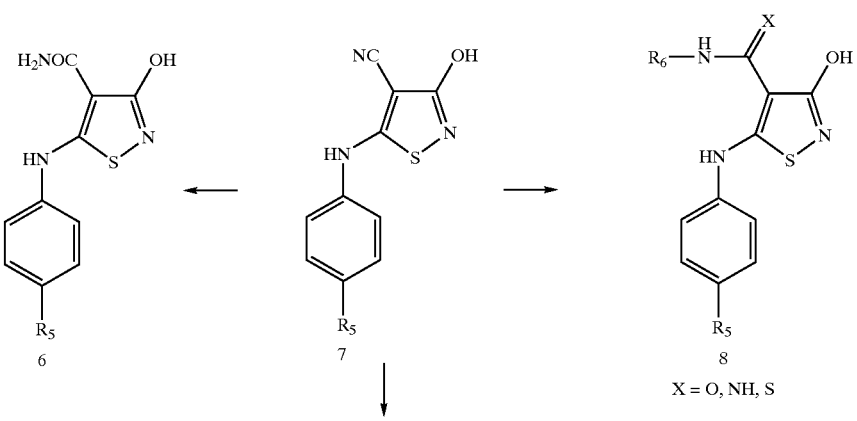

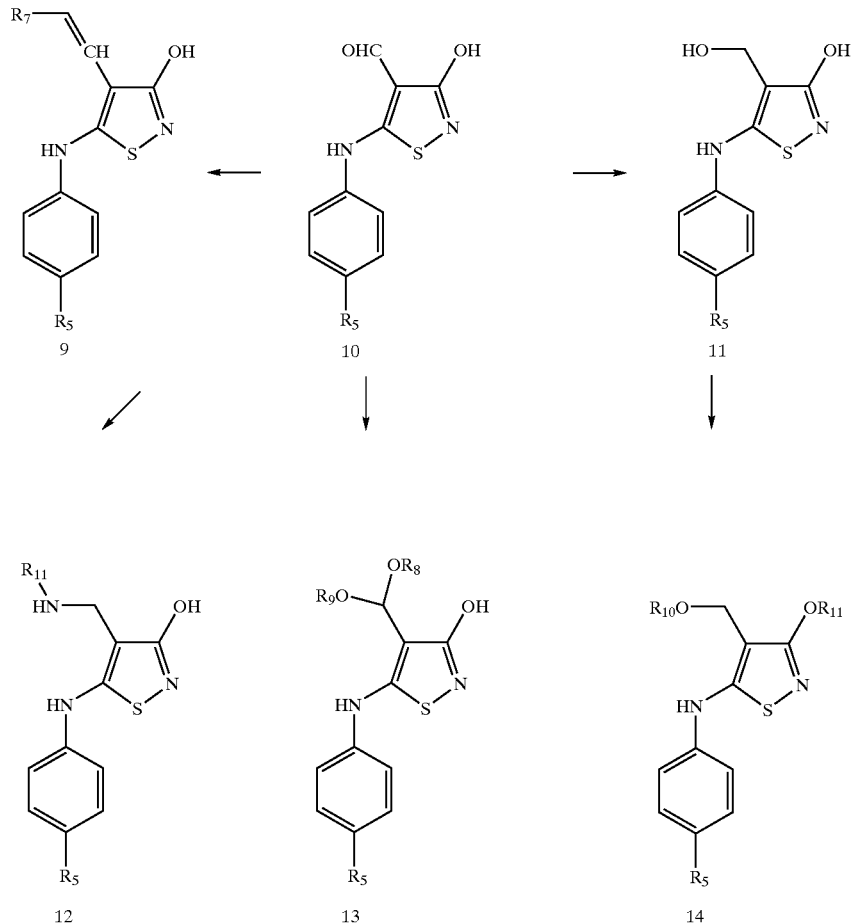

Scheme 3 depicts a further exemplary route in which the aldehyde compound 10 is oxidized with an oxidant (e.g., silver oxide) to give the corresponding carboxylic acid compound 15, which may be further converted to an ester compound 16 (X=O) or an amide compound 17 (X=NH) by reacting it with an alcohol or amine in the presence of a carboxyl group activating reagent, such as 1,3-dicarboxyl-carbodiimide.

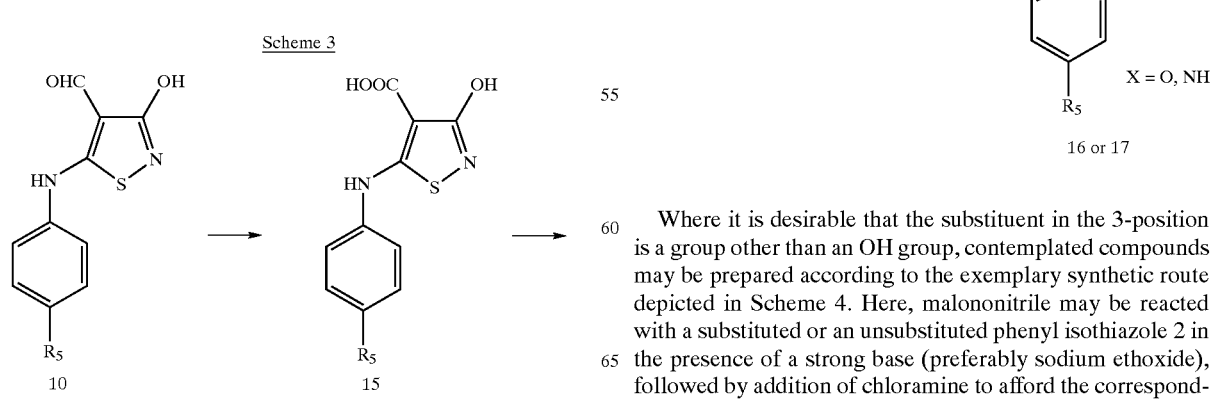

Where it is desirable that the substituent in the 3-position is a group other than an OH group, contemplated compounds may be prepared according to the exemplary synthetic route depicted in Scheme 4. Here, malononitrile may be reacted with a substituted or an unsubstituted phenyl isothiazole 2 in the presence of a strong base (preferably sodium ethoxide), followed by addition of chloramine to afford the corresponding isothiazole compound 18. In step 2, the amino group of the isothiazole compound 18 may be converted to an alkylamino group by reductive amination using an aldehyde to afford compound 19 or to an amide 20 using a carboxylic acid and a coupling agent (e.g., 1,3-dicyclohexylcarbodiimide or N'-(ethylcarbonimidoyl)-N,N-dimethyl-, monohydrochloride) in step 3. Alternatively, as shown in step 4, isothiazole compound 18 is reacted with an alkyl isocyanate to give urea derivative 21 (X=NH), or with an alkyl chloroformate to give carbamate compound 22 (X=O).

refers to over expression, under expression, mutation or other change in a protein kinase polypeptide or polypeptide complex that results in an under active, overactive or constitutively active form of the protein kinase.

Consequently, particularly contemplated diseases include various neoplastic diseases, cell proliferative diseases, and viral infections (especially where the immune system is skewed towards a particular Th1 or Th2 phenotype). For example, contemplated neoplastic diseases include carcino-

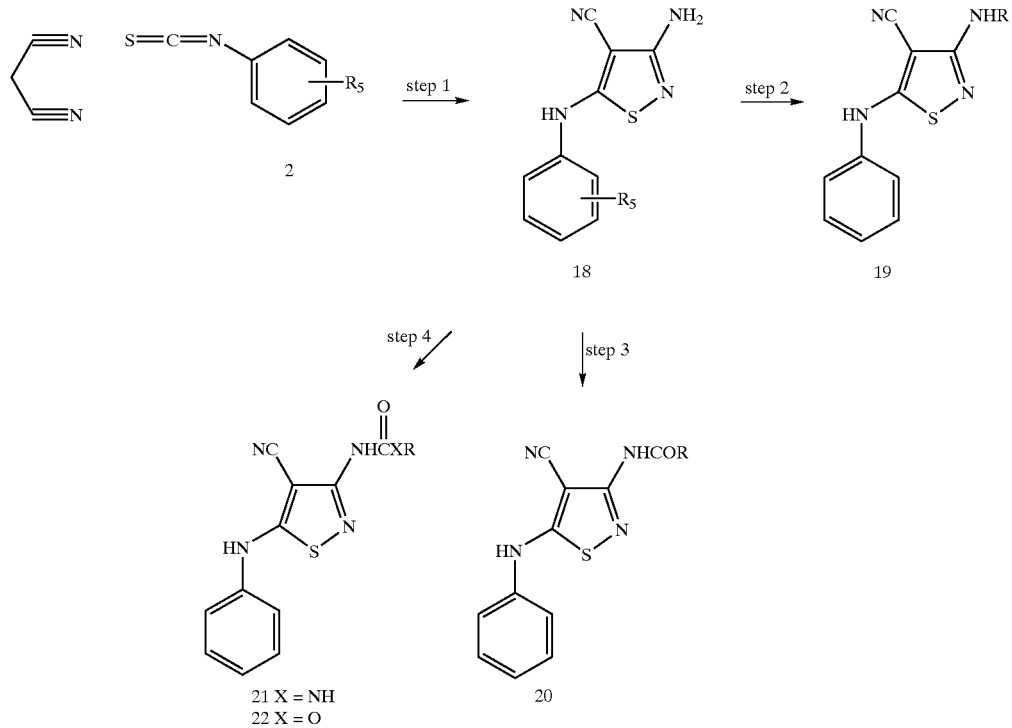

Alternatively, 5-alkylaminoisothiazoles may be prepared from 3-hydroxy-5-methane-sulfonyl-isothiazole-4-carbonitrile and nucleophilic amines as depicted in Scheme 5.

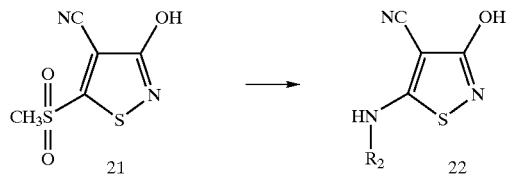

Contemplated Uses

Numerous compounds according to the inventive subject matter have shown significant activity in the inhibition of protein kinases, and especially against MEK/ERK kinase (supra). It is therefore generally contemplated that the compounds according to the inventive subject matter may be employed in the treatment of diseases that are associated with dysregulated activity of protein kinases. The term "dysregulated activity of protein kinases" as-used herein mas of the bladder, breast, colon, kidney, liver, and lung, including small cell lung cancer, esophagus, gall bladder, ovary, pancreas, stomach, cervix, thyroid, prostate, and skin, including squamous cell carcinoma. Other neoplastic diseases include hematopoietic tumors of the lymphoid lineage (e.g., leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, Burkett's lymphoma) and hematopoietic tumors of the myeloid lineage (e.g., acute and chronic myelogenous leukemias, myelodysplastic syndrome and promyelocytic leukemia), tumors of the mesenchymal origin (e.g., fibrosarcoma), tumors of the central and peripheral nervous system (e.g., astrocytoma, glioma, or neuroblastoma), and other tumors, including melanoma, seminoma, teratocarcinoma, osteosarcoma, xeroderma pigmentosum, Kaposi sarcoma, and thyroid follicular cancer. Further examples for cell proliferative diseases include benign prostate hyperplasia, psoriasis, arthritis, and post-surgical stenosis and restenosis.

However, in further contemplated aspects, diseases other than neoplastic diseases and cell proliferative disorders may also be treated with the compounds according to the inventive subject matter. For example, contemplated compounds may be effective as modulators of apoptosis, and may also be useful in the treatment of viral infections, prevention of AIDS development in HIV-infected individuals, autoimmune diseases and neurodegenerative disorders. Yet further contemplated uses of the present compounds include treatment of a patient to inhibit tumor angiogenesis and metastasis.

Depending on the particular compound, it should be recognized that the type and/or specificity of the compound towards a particular kinase might vary considerably. However, it is generally contemplated that all protein kinases (preferably those involved in cell signaling, and most preferably MEK and/or ERK) may be inhibited by contemplated compounds. For example, suitable kinases include cyclin dependent kinases, as well as kinases including Aurora-A, PLK, EGFR, ERBB2, PDGFR, AKT1, IGF1R, VEGFR, TIE2, EPHB4, SRC, FAK, FGF, Abl, IKK, PKC (in various isoforms), and MAP kinases (e.g., MEK, ERK, P38, JNK, MKK). Moreover, while it is generally preferred that the compounds exhibit relatively high selectivity towards a particular kinase or kinase family, it should also be recognized that suitable compounds may have a broad-spectrum inhibitory activity against multiple protein kinases.

Thus, it is particularly contemplated that contemplated compounds are administered to a patient at a concentration effective to reduce protein kinase activity in the patient. The term "reduce protein kinase activity" as used herein refers to any reduction of at least one protein kinase as compared to the activity of the same kinase(s) prior to exposure with the compound, its metabolite, or its prodrug.

Where contemplated compounds are administered in a pharmacological composition, it is contemplated that suitable compounds can be formulated in admixture with a pharmaceutically acceptable carrier. For example, contemplated compounds can be administered orally as pharmacologically acceptable salts, or intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished by minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient. Suitable pharmacological compositions are well known in the art and it should be appreciated that a person of ordinary skill in the art will be readily able to prepare such formulations. Exemplary guidelines may be found in Drug Formulation by I. Racz (John Wiley & Sons; ISBN: 0471905178), or in Drug Products for Clinical Trials: An Intl Guide to Formulation, Production, Quality Control by Donald C. Monkhouse and Christopher T. Rhodes (Marcel Dekker; ISBN: 082479852X).

In certain pharmaceutical dosage forms, prodrug forms of contemplated compounds may be formed for various purposes, including reduction of toxicity, increasing the organ or target cell specificity, etc. One of ordinary skill in the art will readily recognize how to modify the present compounds to pro-drug forms to facilitate delivery of active compounds to a target site within the host organism or patient (see above). One of ordinary skill in the art will also take advantage of favorable pharmacokinetic parameters of the pro-drug forms, where applicable, in delivering the present compounds to a targeted site within the host organism or patient to maximize the intended effect of the compound. For example, where the prodrug is specifically delivered to a cancer target cell, suitable methods and approaches are described in Enzyme-Prodrug Strategies for Cancer Therapy by Roger G. Melton, Richard J. Knox (Plenum Pub Corp; ISBN: 0306458950). Further suitable prodrug forms are described in Pro-drugs as novel drug delivery systems: A symposium (The Society; ISBN: 0841202915).

In addition, contemplated compounds may be administered alone or in combination with other agents for the treatment of various diseases or conditions. Combination therapies according to the present invention comprise the administration of at least one compound of the present invention or a functional derivative thereof and at least one other pharmaceutically active ingredient. The active ingredient(s) and pharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect.

Among other contemplated agents for combination with contemplated compounds, it is especially preferred that such agents include antineoplastic agents, antiviral agents, and/or immunomodulatory agents. For example, suitable agents include interferon, and particularly IFN-alpha, IFN-beta, or IFN-gamma (or fragments or recombinant forms thereof), IL-12, nucleoside analogs, and/or various other kinase inhibitors. Further examples for combination with contemplated compounds include including mitotic inhibitors (e.g., vinblastine), alkylating agents (e.g., cis-platin, carboplatin, or cyclophosphamide), anti-metabolites (e.g., 5-fluorouracil, cytosine arabinoside, or hydroxyurea), growth factor inhibitors, cell cycle inhibitors, intercalating antibiotics (e.g., adriamycin or bleomycin), enzymes, and/or anti-hormones (e.g., anti-estrogens such as Tamoxifen or anti-androgens such as 4'-cyano-3-(4-fluorophenylsulphonyl)-2-hydroxy-2-methyl-3'-(trifluoromethyl)propionanilide)).

Consequently, the inventors contemplate a method of treating a mammalian cell in which the mammalian cell is presented with a compound according to Formula 1 or 2 at a concentration that is effective to inhibit a kinase, and most preferably a MEK kinase. The term "inhibit a kinase" as used herein refers to a reduction in catalytic activity of a kinase in the presence of contemplated compounds as compared to the same kinase in the absence of contemplated compounds. Thus, inhibition may include competitive inhibition, non-competitive inhibition, and/or allosteric inhibition. In further preferred aspects, the cell is a neoplastic cell (in vitro or in vivo), and depending on the particular system, it should be recognized that the compound might also be in a prodrug form (supra).

Consequently, contemplated methods also especially include a method of treating a patient in which in one step the patient is diagnosed as having a condition associated with a dysfunction of MEK. In another step, a composition comprising contemplated compounds is administered to the patient at a dosage effective to treat the condition. Especially contemplated conditions include various cancers (e.g., brain cancer, lung cancer, squamous cell cancer, bladder cancer, gastric cancer, pancreatic cancer, breast cancer, head and neck cancer, renal cancer, prostate cancer, colorectal cancer, esophageal cancer, or thyroid cancer), hyperproliferative diseases (e.g., benign skin or prostate hyperplasia, proliferative glomerulonephritis, etc), and other MEK/ERK-associated diseases, including pancreatitis, diabetes-induced renal disease, leukemia, asthma, rheumatoid arthritis, atherocerosis, psoriasis, excema, scleroderma, diabetes, diabetic retinopathy, premature retinopathy, macular degeneration, hemangioma, glioma, melanoma, Kaposi's sarcoma, restenosis, stroke, heart failure, and immunodeficiency disorders.

EXAMPLES

The following synthetic routes are given to illustrate exemplary strategies for synthesis of contemplated compounds. However, it should be appreciated that numerous modifications of the reagents may result in the numerous corresponding inhibitors. Consequently, the examples below are given only to provide exemplary guidance to a practitioner.

Chloramine

Chlorine gas (3.67 g, 0.052 mole) was passed into a mixture of ice (40 g) and 25% aqueous sodium hydroxide solution (25 ml) in an ice-water bath. With stirring the mixture was treated with an ice-cold 10% aqueous ammonium hydroxide solution (23 ml) portion wise. After the exothermic reaction was complete, the volume of the mixture was diluted to 125 ml with ice water.

3-Hydroxy-5-phenylamino-isothiazol-4-carbonitrile

Method 1: To a cooled suspension of finely ground potassium hydroxide (0.337 g, 6 mmol) in DMF (8 ml) was added cyanoacetamide (0.505 g, 6 mmol) followed by addition of 4-methoxyphenyl isothiocyanate (0.83 ml, 6 mmol). The reaction mixture was stirred at room temperature for 24 hours and treated with aqueous chloramine (30 ml) at 0° C. The mixture was stirred at room temperature for 12 hours, and evaporated to give a residue, which was partitioned between water and EtOAc. The aqueous layer was washed with EtOAc twice and cooled to 0° C. and acidified with 1N HCl solution to pH~3. The precipitate was filtered and washed with water and dried in vacuo to afford a yellow powder (0.95 g, 73%).

Method 2: To a cooled suspension of finely ground potassium hydroxide (0.337 g, 6 mmol) in DMF (8 ml) was added cyanoacetamide (0.505 g, 6 mmol) followed by addition of 4-methoxyphenyl isothiocyanate (0.83 ml, 6 mmol). The reaction mixture was stirred at room temperature for 16 hours and concentrated to give a syrup, which was diluted with water and acidified with 1 N HCl aqueous solution. The suspension was filtered and the solid was washed with water and dried in vacuo. The dried solid was dissolved in EtOAc (30 ml) and a solution of bromine (0.31 ml, 6 mmol) in EtOAc (25 ml) was added drop wise into the mixture. After 1 hour stirring at room temperature the reaction mixture was filtered and the solid was washed with EtOAc and dried in vacuo to afford a yellow powder (0.86 g, 66%).

3-Hydroxy-5-(4-styryl-phenylamino)-isothiazole-4-carbonitrile

The title compound was prepared from 1-isothiacyanato-4-styryl-benzene and 2-cyanoacetamide by the procedure analogous to Method 2 for 3-Hydroxy-5-phenylamino-isothiazol-4-carbonitrile. $^1$H NMR (300 MHz, DMSO-d$_6$) δ: 7.22–7.65 (m, 11H). MS (ES, m/z): 320.3, [M-H]$^+$, 318.1 [M-H]$^-$.

3-Hydroxy-5-(4-piperidin-1-yl-phenylamino)-isothiazole-4-carbonitrile

The title compound was prepared from 1-isothiacyanato-4-piperidin-1-yl-benzene and 2-cyanoacetamide by the procedure analogous to Method 2 for 3-Hydroxy-5-phenylamino-isothiazol-4-carbonitrile. $^1$H NMR (CD3OD) δ: 7.15 (d, 2H); 6.96 (d, 2H); 7.15 (d, 2H); 3.15 (t, 4H); 1.6–1.74 (m, 6H). MS (ES, m/z): 301.2, [M-H]$^+$, 299.5 [M-H]$^-$.

3-Hydroxy-5-(3-cyano-phenylamino)-isothiazole-4-carbonitrile

The title compound was prepared from 1-isothiacyanato-3-cyano-benzene and 2-cyanoacetamide by the procedure analogous to Method 2 for 3-Hydroxy-5-phenylamino-isothiazol-4-carbonitrile. $^1$H NMR (CD3OD) δ: 7.5–7.7 (m, 4H) ppm; MS (ES, m/z): 242.9, [M-H]$^+$, 241.1 [M-H]$^-$.

3-Hydroxy-5-(4-isopropyl-phenylamino)-isothiazole-4-carbonitrile

The title compound was prepared from 1-isothiacyanato-4-isopropyl-benzene and 2-cyanoacetamide by the procedure analogous to Method 2 for 3-Hydroxy-5-phenylamino-isothiazol-4-carbonitrile. $^1$H NMR (CD3OD) δ: 7.2–7.4 (m, 4H); 2.9 (q, 1H); 1.24 (d, 6H); MS (ES, m/z): 259.8, [M-H]$^+$, 258.3 [M-H]$^-$.

3-Methoxy-5-phenylamino-isothiazol-4-carbonitrile

To a solution of 3-hydroxy-5-phenylamino-isothiazol-4-carbonitrile (2.82 g, 13 mmol), triphenylphosphine (4.04 g, 15.6 mmol), methanol (0.53 ml) in THF (25 ml) was added diethyl azadicarboxylate (DEAD, 2.46 ml, 15.6 mmol) at 0° C. The mixture was stirred at ambient temperature and evaporated to give a residue. The crude product was purified on silica gel (hexane/EtOAc, 1:1) to give a yellow powder (1.26 g, 42%).

3-Amino-5-phenylamino-isothiazol-4-carbonitrile

To an ice-cold solution of sodium ethoxide (1.7 g, 25 mmol) in absolute ethanol (25 ml) was added malononitrile (1.65 g, 25 mmol), followed by addition of phenyl isothiocyanate (5.43 g, 25 mmol). The mixture was stirred at ambient temperature for 12 hours, cooled and then treated with freshly prepared aqueous chloramine solution (125 ml). After being stirred for 24 hours at ambient temperature, the mixture was filtered and the solid was dried in air. Crystallization from DMF-EtOH afforded colorless crystals (2.5 g, 65%).

3-Benzylamino-5-phenylamino-isothiazol-4-carbonitrile

Sodium borohydride (4.12 g, 1.09.1 mmol) was added portion wise to a mixture of 3-amino-5-phenylamino-isothiazole-4-carbonitrile (1.57 g, 7.27 mmol), sodium acetate trihydrate (2.97 g, 21.81 mmol) and benzaldehyde (0.74 ml, 7.27 mmol) in acetic acid (2.3 ml), water (9 ml) and ethanol (7 ml) at 0° C. The solution was stirred at ambient temperature for 30 minutes, and then diluted with ethyl acetate (EtOAc) (55 ml). The organic layer was washed with a 10% solution of sodium hydroxide (3×35 ml) and brine (35 ml), dried and evaporated to give an oil, which was purified on silica gel (hexane/EtOAc, 1:1) to afford a solid (1.45 g, 65%).

Determination of in vivo Inhibition of MEK and/or ERK by Contemplated Compounds Activities of compounds were determined using a cell-based assay system. 293T cells were engineered to express a luciferase reporter protein in response to activation of ERK. ERK was activated by the doxycycline inducible expression of a constitutively activated mutant MEK. The activated MEK mutant had serines 218 and 222 replaced with aspartic acids. Therefore, addition of doxycycline to the media of cells induced an increase in MEK-ERK dependent luciferase expression.

Cells were plated at 5000 cells per well of a 384 well plate in 20 ul of media containing 10 ng/ml doxycycline. Compounds were resuspended in DMSO at a concentration of 20 mM. These compound stocks were diluted at least 200 fold so the concentration of DMSO was never above 0.5%. Cells were incubated with compounds for 24 hours at which time 25 ul of Steady-Glo (Promega Corp.) was added. The plates were then assayed for luminescence. Percent inhibition was calculated by dividing the luminescence of compound treated cells by control cells.

Determination of In Vitro Inhibition of MEK and/or ERK By Contemplated Compounds In order to identify ideal inhibitory compounds in a high throughput-screening (HTS) format a 96-well radiolabel incorporation format assay utilizing purified GST-hMEK1 and mERK2 enzymes was developed. Compounds were diluted from dimethylsulfoxide (DMSO) stocks into 1× Simplified Assay Buffer (SAB) (20 mM HEPES and 10 mM $MgCl_2$). A typical 25 microliter assay contained 0.002 nanomoles $MEK^{CA}$, 0.02 nanomoles ERK, 0.25 nanomoles MBP, 0.25 nanomoles unlabeled ATP, and 0.1 $\mu$Ci [$\gamma^{33}P$] ATP. The screening assay essentially comprised four additions. Five $\mu$l of diluted compound were dispensed to 96-well assay plates. Ten $\mu$l of 2.5× enzyme cocktail ($MEK^{CA}$ and ERK only) were then added to each well followed by a pre-incubation for 15 minutes at 37° C. Ten $\mu$l of 2.5× substrate cocktail (labeled and unlabeled ATP plus MBP) were then added, followed by incubation for one hour at 37° C. Finally, 200 $\mu$l of 10% trichloroacetic acid (TCA) were added and incubated for 30 minutes to halt the reaction and precipitate radio labeled protein products. A filter plate was placed in the Filtermate Harvester, wetted twice with water, and rinsed twice with 1% pyrophosphate to block nonspecific binding to the glass filter. An assay plate was then scanned and aspirated or harvested onto the filter plate. The filter plate was then washed 12 times with water. Water was displaced by two washes with absolute ethanol and the plate was removed and allowed to air dry for 30 minutes at room temperature. A back seal was applied manually and 40 $\mu$l of scintillation cocktail were dispensed per well. A top seal was applied and the plate was counted in the TopCount for two seconds per well.

Results for MEK Inhibition

The following exemplary compounds were tested in vitro and in vivo for their biological activity, and especially for their activity in inhibition of MEK kinase. The following table depicts selected compounds and their activities. $EC_{50}$ is the minimum concentration causing 50% inhibition in cell-based assays; $IC_{50}$ is the minimum concentration causing 50% inhibition in vitro assays and NT means "not tested", wherein A refers to an inhibitory concentration of less than 10 microM, B refers to an inhibitory concentration of 10 microM to 100 microM, and C refers to an inhibitory concentration of greater than 100 microM.

| Compound | Structure | $EC_{50}$ | $IC_{50}$ |
|---|---|---|---|
| 1 | 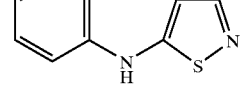 | B | A |
| 2 | 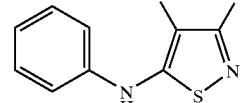 | A | B |
| 3 | 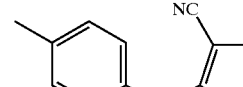 | A | B |
| 4 | 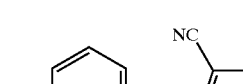 | B | B |
| 5 | 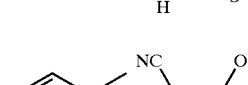 | B | B |
| 6 | 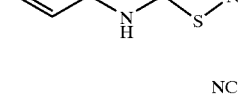 | C | NT |
| 7 | 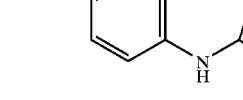 | C | NT |
| 8 | 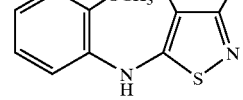 | C | NT |

-continued

| Compound | Structure | EC$_{50}$ | IC$_{50}$ |
|---|---|---|---|
| 9 | 4-Cl-C$_6$H$_4$-NH- isothiazole (CN, OH) | C | B |
| 10 | 3-Cl-C$_6$H$_4$-NH- isothiazole (CN, OH) | C | B |
| 11 | 2-Cl-C$_6$H$_4$-NH- isothiazole (CN, OH) | C | B |
| 12 | 4-O$_2$N-C$_6$H$_4$-NH- isothiazole (CN, OH) | C | A |
| 13 | 1-naphthyl-NH- isothiazole (CN, OH) | A | A |
| 14 | 4-Ph-2-OCH$_3$-C$_6$H$_3$-NH- isothiazole (CN, OH) | C | A |
| 15 | 4-iPr-C$_6$H$_4$-NH- isothiazole (CN, OH) | A | A |
| 16 | 2,6-diisopropylphenyl-NH- isothiazole (CN, OH) | B | B |

-continued

| Compound | Structure | EC$_{50}$ | IC$_{50}$ |
|---|---|---|---|
| 17 | N-methyl-naphthyl-NH- isothiazole (CN, OH) | A | A |
| 18 | 4-(dimethylamino)naphthyl-NH- isothiazole (CN, OH) | A | A |
| 19 | 2-CF$_3$-C$_6$H$_4$-NH- isothiazole (CN, OH) | NT | B |
| 20 | 4-methylphenyl-NH- isothiazole (CN, NH$_2$) | NT | A |
| 21 | 4-H$_2$N-C$_6$H$_4$-NH- isothiazole (CN, OH) | NT | A |
| 22 | 4-Ac-C$_6$H$_4$-NH- isothiazole (CN, OH) | NT | A |
| 23 | 4-Cl-3-CF$_3$-C$_6$H$_3$-NH- isothiazole (CN, OH) | NT | A |
| 24 | 4-Br-C$_6$H$_4$-NH- isothiazole (CN, OH) | NT | A |
| 25 | 4-(methoxycarbonyl)-C$_6$H$_4$-NH- isothiazole (CN, OH) | NT | A |

-continued

| Compound | Structure | EC$_{50}$ | IC$_{50}$ |
|---|---|---|---|
| 26 | 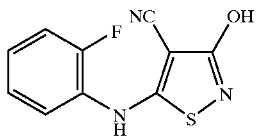 | NT | A |
| 27 | 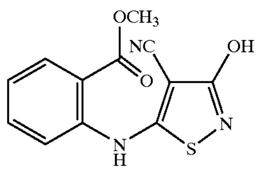 | NT | A |
| 28 | 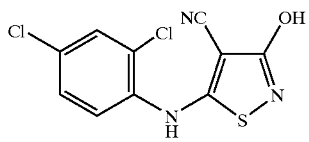 | NT | A |
| 29 | 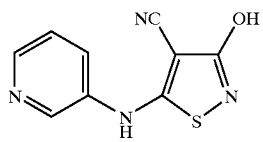 | NT | A |
| 30 | 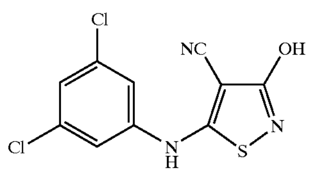 | NT | A |
| 31 | 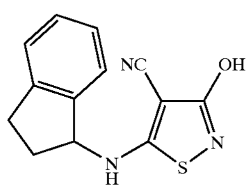 | NT | A |
| 32 | 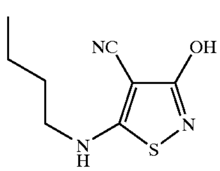 | NT | A |
| 33 | 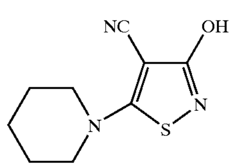 | NT | A |
| 34 | 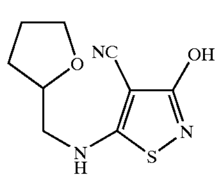 | NT | A |

-continued

| Compound | Structure | EC$_{50}$ | IC$_{50}$ |
|---|---|---|---|
| 35 | 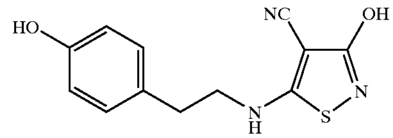 | NT | A |
| 36 | 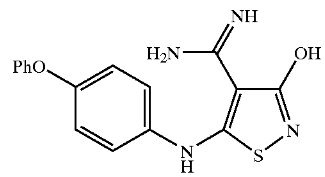 | NT | A |
| 37 | 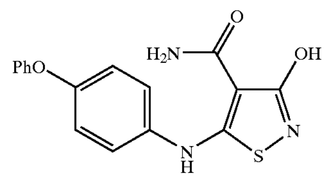 | NT | A |
| 38 | 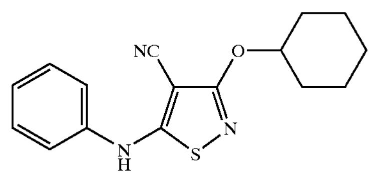 | NT | A |
| 39 | 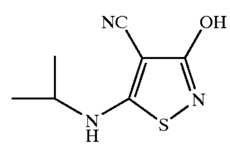 | NT | A |
| 40 | 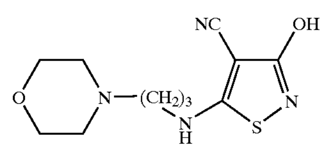 | NT | A |

Thus, specific embodiments and applications of protein kinase inhibitors have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A compound selected from the group consisting of the following, or a salt thereof:
5-(3-methylphenyl)amino-3-hydroxy-4-cyano-isothiazole;
5-(4-methoxyphenyl)amino-3-hydroxy-4-cyano-isothiazole;

5-(2-methoxyphenyl)amino-3-hydroxy-4-cyano-isothiazole;
5-(3-methoxyphenyl)amino-3-hydroxy-4-cyano-isothiazole;
5-(2-chlorophenyl)amino-3-hydroxy-4-cyano-isothiazole;
5-(4-nitrophenyl)amino-3-hydroxy-4-cyano-isothiazole;
5-(1-naphthyl)amino-3-hydroxy-4-cyano-isothiazole;
5-(4-phenyl-2-methoxyphenyl)amino-3-hydroxy-4-cyano-isothiazole;
5-(2,6-di-isopropylphenyl)amino-3-hydroxy-4-cyano-isothiazole;
5-(2-dimethylamino-1-naphthyl)amino-3-hydroxy-4-cyano-isothiazole;
5-(4-dimethylamino-1-naphthyl)amino-3-hydroxy-4-cyano-isothiazole;
5-(2-trichloromethyl-phenyl)amino-3-hydroxy-4-cyano-isothiazole;
5-(4-aminophenyl)amino-3-hydroxy-4-cyano-isothiazole;
5-(4-acetyl-phenyl)amino-3-hydroxy-4-cyano-isothiazole;
5-(4-methoxycarbonyl-phenyl)amino-3-hydroxy-4-cyano-isothiazole;
5-(2-fluorophenyl)amino-3-hydroxy-4-cyano-isothiazole;
5-(2-methoxycarbonyl-phenyl)amino-3-hydroxy-4-cyano-isothiazole;
5-(2,4-dichlorophenyl)amino-3-hydroxy-4-cyano-isothiazole;
5-(1-indanyl)amino-3-hydroxy-4-cyano-isothiazole;
5-(pyridin-3-yl)amino-3-hydroxy-4-cyano-isothiazole;
5-(4-chlorophenyl)amino-3-hydroxy-4-cyano-isothiazole;
5-(3-chlorophenyl)amino-3-hydroxy-4-cyano-isothiazole;
5-(3-trichloromethyl-4-chlorophenyl)amino-3-hydroxy-4-cyano-isothiazole;
5-(3,5-dichlorophenyl)amino-3-hydroxy-4-cyano-isothiazole; and
5-(4-bromophenyl)amino-3-hydroxy-4-cyano-isothiazole.

2. A compound selected from the group consisting of the following, or a salt thereof:

5-(4-chlorophenyl)amino-3-hydroxy-4-cyano-isothiazole;
5-(3-chlorophenyl)amino-3-hydroxy-4-cyano-isothiazole;
5-(3-trichloromethyl-4-chlorophenyl)amino-3-hydroxy-4-cyano-isothiazole;
5-(3,5-dichlorophenyl)amino-3-hydroxy-4-cyano-isothiazole; and
5-(4-bromophenyl)amino-3-hydroxy-4-cyano-isothiazole.

* * * * *